US012629460B2

(12) United States Patent
Cheng et al.

(10) Patent No.: US 12,629,460 B2
(45) Date of Patent: *May 19, 2026

(54) USE OF A CELL CULTURE COMPOSITION FOR PROMOTING CELL GROWTH

(71) Applicant: TAIWAN MITOCHONDRION APPLIED TECHNOLOGY CO., LTD., Zhubei City (TW)

(72) Inventors: Han-Chung Cheng, Zhubei City (TW); Chih-Kai Hsu, Zhubei City (TW); Hui-Ching Tseng, Zhubei City (TW); Shun-Chieh Yang, Zhubei City (TW); Chi-Tang Tu, Zhubei City (TW); Szu-Ting Liu, Zhubei City (TW); Li-Hsin Yao, Zhubei City (TW)

(73) Assignee: TAIWAN MITOCHONDRION APPLIED TECHNOLOGY CO., LTD., Zhubei City (TW)

( * ) Notice: Subject to any disclaimer, the term of this patent is extended or adjusted under 35 U.S.C. 154(b) by 786 days.

This patent is subject to a terminal disclaimer.

(21) Appl. No.: 17/947,994

(22) Filed: Sep. 19, 2022

(65) Prior Publication Data

US 2023/0023218 A1      Jan. 26, 2023

Related U.S. Application Data

(63) Continuation-in-part of application No. PCT/CN2021/081854, filed on Mar. 19, 2021.

(60) Provisional application No. 62/992,546, filed on Mar. 20, 2020.

(51) Int. Cl.
| | |
|---|---|
| *A61M 1/02* | (2006.01) |
| *A61K 35/12* | (2015.01) |
| *A61K 35/16* | (2015.01) |
| *A61K 35/19* | (2015.01) |
| *A61K 35/28* | (2015.01) |
| *A61K 38/36* | (2006.01) |
| *A61M 1/36* | (2006.01) |
| *A61P 13/12* | (2006.01) |
| *A61P 17/02* | (2006.01) |
| *A61P 19/02* | (2006.01) |
| *A61P 19/04* | (2006.01) |
| *C12N 5/00* | (2006.01) |
| *C12N 5/073* | (2010.01) |
| *C12N 5/0775* | (2010.01) |

(52) U.S. Cl.
CPC ............. *A61M 1/029* (2013.01); *A61K 35/12* (2013.01); *A61K 35/16* (2013.01); *A61K 35/19* (2013.01); *A61K 35/28* (2013.01); *A61K 38/36* (2013.01); *A61M 1/3693* (2013.01); *A61P 13/12* (2018.01); *A61P 17/02* (2018.01); *A61P 19/02* (2018.01); *A61P 19/04* (2018.01); *C12N 5/0018* (2013.01); *C12N 5/0605* (2013.01); *C12N 5/0667* (2013.01); *C12N 2500/84* (2013.01); *C12N 2501/998* (2013.01); *C12N 2502/115* (2013.01)

(58) Field of Classification Search
None
See application file for complete search history.

(56) References Cited

U.S. PATENT DOCUMENTS

| | | | | |
|---|---|---|---|---|
| 5,834,418 A | * | 11/1998 | Brazeau | A61K 35/19 530/380 |
| 6,100,068 A | * | 8/2000 | Paik | C07K 14/005 435/69.3 |
| 10,732,172 B1 | * | 8/2020 | Ingber | G01N 33/5064 |
| 2018/0057610 A1 | * | 3/2018 | Mccully et al. | A61K 49/1896 |

* cited by examiner

*Primary Examiner* — Blaine Lankford
(74) *Attorney, Agent, or Firm* — Maschoff Brennan

(57) ABSTRACT

The embodiments of the present disclosure provide a cell culture composition and a use thereof, and the cell culture composition includes a culture medium and mitochondria. The cell culture composition including mitochondria can promote cell growth and improve the function of the damaged or aged stem cells, thereby improving overall cell growth.

11 Claims, 7 Drawing Sheets

ARPE-19

ARPE-19

HepG2

MDCK

USE OF A CELL CULTURE COMPOSITION FOR PROMOTING CELL GROWTH

CROSS-REFERENCE TO RELATED APPLICATIONS

This application is a continuation-in-part of International Application No. PCT/CN2021/081854, filed on Mar. 19, 2021, which claiming priority to U.S. provisional patent application Ser. No. 62/992,546, filed on Mar. 20, 2020, the entire contents of which are hereby incorporated by reference.

BACKGROUND

1. Technical Field

The present disclosure relates to a use of a cell culture composition, specifically, to a use of a cell culture composition including mitochondria.

2. Related Art

Cell culture medium is a basic nutrient composition that simulates the cell growth environment in animals and plants, and it provides essential nutrients that cells cannot synthesize and maintains appropriate pH and osmolality so that cells can survive and proliferate in vitro. During cell growth, in order to increase the growth efficiency and improve the function of cells, some auxiliary supplements may be added.

In the minimal culture medium or severe culture condition, the cell growth is slow, and the cultured cells may be weak, less viable, or even unable to grow. If the cultured cells are not healthy enough or grow too slowly, it may adversely affect the subsequent experiment or research.

SUMMARY

In one embodiment of the present disclosure, a use of a cell culture composition for promoting cell growth is provided, wherein the cell culture composition comprises a culture medium and mitochondria.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

Figure 1A:
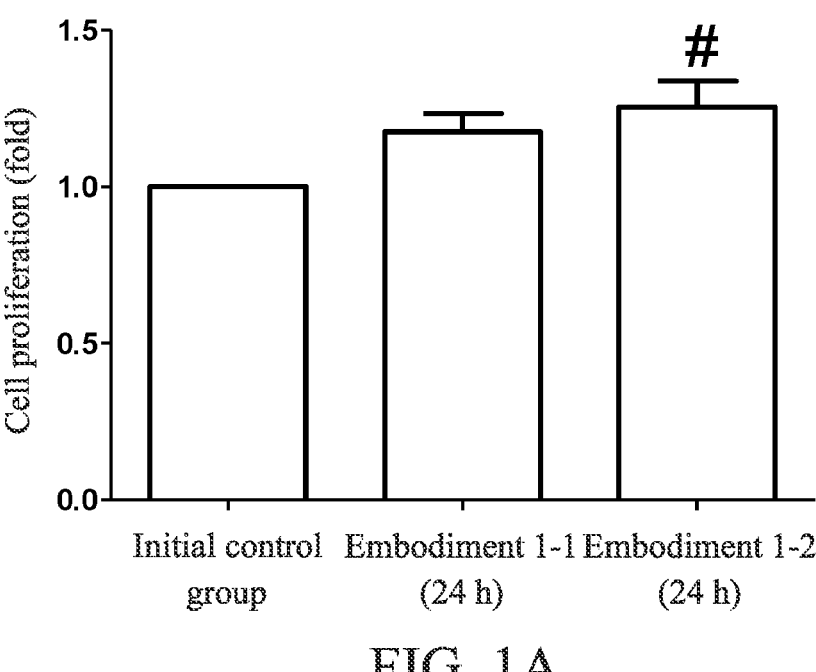
FIGS. 1A and 1B show the cell proliferation of ARPE-19 cultured by the cell culture composition according to the embodiment of the present disclosure for 24 hours (FIG. 1A) and for 48 hours (FIG. 1B)

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the present disclosure. The following embodiments further illustrate various aspects of the present disclosure, but are not meant to limit the scope of the present disclosure.

Mitochondria are places where oxidative phosphorylation (OXPHOS) and adenosine triphosphate (ATP) synthesis occur. In addition to supplying the energy for normal cell metabolism, the mitochondria are also responsible for regulating the functions including dealing with the oxidative stress in cells, signaling, and so on. During cell culture, the function of the mitochondria is considerably related to cell growth. The poor function of mitochondria leads to less efficiency in energy production and causes the cells to grow slowly or poorly. Therefore, the inventor adds the mitochondria as a supplement to the cell culture medium to improve the cell growth.

According to one embodiment of the present disclosure, the cell culture composition includes a culture medium and mitochondria. The cell culture composition may be liquid at normal temperature and normal pressure, and it may be stored at room temperature, preferably at 4° C.

The culture medium may include DMEM, F12, DMEM/F12, MEM, MEM-a, Keratinocyte SFM (1X), IMEM, RPMI 1640, M-199, Opti-MEM, Ham's F-10 Nutrient Mixture, Ham's F-12 Nutrient Mixture, or IMDM, but it is not limited thereto. The culture medium may be liquid or solid. The culture medium may be selected depending on the cultured cells, and appropriate nutrient additives and water may be added.

The mitochondria may be taken from animal cells or plant cells, but it is not limited thereto. In some embodiments of the present disclosure, when culturing animal cells, the mitochondria taken from animal cells may be added to the culture medium. The animal cells providing the mitochondria may be any cells having the mitochondria including adipose-derived stem cells, monocytes, embryonic stem cells, mesenchymal stem cells, hematopoietic stem cells, CD34+ stem cells, bone marrow stem cells, skeletal muscle cells, hepatocytes, kidney cells, platelets, fibroblasts, or endothelial cells. In the cell culture composition, the cell culture composition may include 1 µg to 100 µg of the mitochondria per milliliter, but it is not limited thereto. In other embodiments, the cell culture composition may include 5 µg to 80 µg of the mitochondria per milliliter. In other embodiments, the cell culture composition may include 15 µg to 40 µg of the mitochondria per milliliter.

According to other embodiments of the present disclosure, the cell culture composition may include a culture medium, at least one nutrient additive, and mitochondria.

The nutrient additive may include fetal bovine serum (FBS), salts, amino acids, horse serum, human serum, vitamins, glucose, growth factors, proteins, animal-derived extracts, carbohydrates, inositol, mercaptoethanol, or folic acid, but it is not limited thereto. The salts may include sodium salts, potassium salts, magnesium salts, calcium salts, chlorides, carbonates, pyruvates, nitrates, phosphates, or other inorganic salts, but it is not limited thereto. The appropriate nutrient additives may be selected depending on the cultured cell.

According to other embodiments of the present disclosure, the cell culture composition may include a culture medium, mitochondria, and platelets.

The platelets may be the platelets taken from animal blood, but it is not limited thereto. In the cell culture composition, the cell culture composition may include $1\times10^6$ to $1\times10^8$ of the platelets per milliliter, but it is not limited thereto. In other embodiments, the cell culture composition may include $1\times10^8$ of the platelets per milliliter.

According to other embodiments of the present disclosure, the cell culture composition may include a culture medium, mitochondria, and complement component 3 (C3).

In the cell culture composition, the cell culture composition may include 0.1 µg to 20 µg of C3 per milliliter, but it is not limited thereto. In other embodiments, the cell culture composition may include 10 µg of C3 per milliliter.

According to one embodiment of the present disclosure, the cell culture composition may promote cell growth and improve cell proliferation. The cells cultured by the cell culture composition of the present disclosure may include any somatic cells. The somatic cells may include retinal cells, hepatocytes, kidney cells, tenocytes, skin cells, or immunocytes. The immunocytes may include natural killer (NK) cells. The NK cells may express at least one of CD56+, CD3−, CD94+, CD122+, CD127+, KIR+, NKG2A+, NKG2D+, NKp30+, NKp44+, NKp46+, and NKp80+.

According to one embodiment of the present disclosure, the cell culture composition may decrease senescence level of the damaged or aged cells. The cells cultured by the cell culture composition of the present disclosure may include any somatic cells or any stem cells. The somatic cells may include retinal cells, hepatocytes, kidney cells, tenocytes, skin cells, or immunocytes. The stem cells may include mesenchymal stem cells. The mesenchymal stem cells may express at least one of CD44+, CD90+, CD105+, CD106+, CD166+, Stro-1+, and CD34−. The mesenchymal stem cells may be adipose-derived stem cells, umbilical cord stem cells, placental stem cells, bone marrow stem cells, amniotic stem cells, skin stem cells, peripheral blood stem cells, endometrial stem cells, amniotic membrane stem cells, gingival stem cells, or dental pulp stem cells.

The following describes how to prepare the cell culture composition of the present disclosure.

The mitochondria used in one embodiment of the present disclosure are taken from human adipose-derived stem cells (ADSC). The culture medium for the stem cells includes Keratinocyte SFM (1X) solution (Gibco), bovine pituitary extract (BPE, Gibco), and 10% (% w/w) FBS (HyClone). Firstly, ADSCs are cultured in a Petri dish to $1.5\times10^8$ cells and then washed with Dulbecco's phosphate-buffered saline (DPBS). Next, DPBS is removed, trypsin for dissociating adherent cells from the Petri dish surfaces is added and reacted at 37° C. for 3 min, and the reaction is stopped by adding the culture medium for the stem cells. Next, ADSCs are washed down from the Petri dish, dispersed, and centrifuged at 600 g for 10 min, and the supernatant is removed. Next, the remained ADSCs and 80 mL of IBC-1 buffer (225 mM mannitol, 75 mM sucrose, 0.1 mM EDTA, and 30 mM Tris-HCl pH 7.4) are added to a homogenizer, and ADSCs are ground 15 times on ice by the homogenizer. Next, the ground ADSCs are centrifuged at 1000 g for 15 min, and the supernatant is collected in another centrifuge tube and centrifuged again at 9000 g for 10 min. After centrifuging, the supernatant is removed, and the obtained pellets are the mitochondria. Next, 1.5 mL of IBC-2 buffer (225 mM mannitol, 75 mM sucrose, and 30 mM Tris-HCl pH 7.4) and a protease inhibitor are added to the mitochondria, and then the mitochondria are stored at 4° C.

During cell culture, an appropriate culture medium may be selected depending on the cell type, and the required nutrient additives and the mitochondria are then added at the desired concentration and mixed uniformly to prepare the cell culture composition. The cell culture composition is preferably fresh prepared, but it is not limited thereto. The cell culture composition may be prepared in advance and stored at 4° C. until used for performing cell culture.

The following describes the cell culture performed by the cell culture composition of the present disclosure.

Experiment 1: Increasing the Cell Proliferation

In this experiment, human retinal pigment epithelium cells (ARPE-19), hepatocytes (HepG2), Madin-Darby Canine kidney cells (MDCK), human tenocytes, and nature killer cells (NK92MI) are cultured by the cell culture composition of the embodiments of the present disclosure as the cell culture medium. In addition, the effect of the cell culture composition on cell growth is assessed by Alamar blue cell viability reagent kit and expressed by the cell proliferation (fold).

Alamar blue is a reagent for assessing cell viability. Resazurin in the Alamar blue reagent is a redox indicator and is a deep blue dye that is non-toxic, permeable to the cell membrane, and low-fluorescent. When resazurin enters into the healthy cells, it is reduced to resorufin, which is pink and high-fluorescent, due to the reduced environment in the cells. The cell proliferation may be assessed by measuring the absorbance or the fluorescence of resorufin. The higher the absorbance or the fluorescence of resorufin indicates the more cells and the higher cell proliferation. The higher cell proliferation indicates the healthier cells and the better proliferation ability. Therefore, Alamar blue is used as an indicator for assessing cell proliferation or cell viability in this experiment.

The detailed compositions of the cell culture composition of the embodiments used in this experiment are shown in Tables 1 to 5.

For ARPE-19, the culture medium may be DMEM/F12 (Gibco), and the nutrient additives may include 2.5 mM glutamine, 15 mM HEPES, 0.5 mM sodium pyruvate, 1200 mg/L sodium bicarbonate, and 10% FBS. The concentration of the mitochondria in the cell culture composition may be 1 µg/mL to 100 µg/mL, may be 5 µg/mL to 80 µg/mL, may be 15 µg/mL to 40 µg/mL, or may be 15 µg/mL or 40 µg/mL.

For HepG2, the culture medium may be DMEM/F12, and the nutrient additives may include 10% FBS. The concentration of the mitochondria in the cell culture composition may be 1 µg/mL to 100 µg/mL, may be 5 µg/mL to 80 µg/mL, may be 15 µg/mL to 40 µg/mL, or may be 15 µg/mL or 40 µg/mL.

For MDCK, the culture medium may be MEM-a with Earle's balanced salt (Thermo Fisher Scientific), and the nutrient additives may include 5% FBS. The concentration of the mitochondria in the cell culture composition may be 1 µg/mL to 100 µg/mL, may be 5 µg/mL to 80 µg/mL, may be 15 µg/mL to 40 µg/mL, or may be 15 µg/mL or 40 µg/mL.

For human tenocytes, the culture medium may be DMEM/F12, and the nutrient additives may include 10% FBS. The concentration of the mitochondria in the cell culture composition may be 1 µg/mL to 100 µg/mL, may be 5 µg/mL to 80 µg/mL, may be 15 µg/mL to 40 µg/mL, or may be 15 µg/mL or 40 µg/mL.

For NK92MI, the culture medium may be MEM-a with Earle's balanced salt (Thermo Fisher Scientific), and the nutrient additives may include 0.02 mM inositol, 0.1 mM mercaptoethanol, 0.02 mM folic acid, 12.5% FBS, and 12.5% horse serum (HS). The concentration of the mitochondria in the cell culture composition may be 1 µg/mL to 100 µg/mL, may be 5 µg/mL to 80 µg/mL, may be 15 µg/mL to 40 µg/mL, or may be 1 µg/mL, 15 µg/mL, 40 µg/mL, or 100 µg/mL.

TABLE 1

| | Cell | |
| | ARPE-19 | |
| Group | Embodiment 1-1 | Embodiment 1-2 |
|---|---|---|
| Culture medium | DMEM/F12 | |
| Nutrient additive | 2.5 mM glutamine | |
| | 15 mM HEPES | |

TABLE 1-continued

| | Cell | |
| | ARPE-19 | |
| Group | Embodiment 1-1 | Embodiment 1-2 |
|---|---|---|
| | 0.5 mM sodium pyruvate | |
| | 1200 mg/L sodium bicarbonate | |
| | 10% FBS | |
| Mitochondria | 15 µg/mL | 40 µg/mL |

TABLE 2

| | Cell | |
| | HepG2 | |
| Group | Embodiment 2-1 | Embodiment 2-2 |
|---|---|---|
| Culture medium | DMEM/F12 | |
| Nutrient additive | 10% FBS | |
| Mitochondria | 15 µg/mL | 40 µg/mL |

TABLE 3

| | Cell | |
| | MDCK | |
| Group | Embodiment 3-1 | Embodiment 3-2 |
|---|---|---|
| Culture medium | MEM-α with Earle's balanced salt | |
| Nutrient additive | 5% FBS | |
| Mitochondria | 15 µg/mL | 40 µg/mL |

TABLE 4

| | Cell | | | | |
| | Human tenocytes | | | | |
| Group | Comparative example 4 | Embodiment 4-1 | Embodiment 4-2 | Embodiment 4-3 | Embodiment 4-4 |
|---|---|---|---|---|---|
| Culture medium | | | DMEM/F12 | | |
| Nutrient additive | | | 10% FBS | | |
| Mitochondria | — | 1 µg/mL | 15 µg/mL | 40 µg/mL | 100 µg/mL |

TABLE 5

| | Cell | | | | |
| | NK92MI | | | | |
| Group | Comparative example 5 | Embodiment 5-1 | Embodiment 5-2 | Embodiment 5-3 | Embodiment 5-4 |
|---|---|---|---|---|---|
| Culture medium | | | MEM-α with Earle's balanced salt | | |
| Nutrient additive | | | 0.02 mM inositol | | |
| | | | 0.1 mM mercaptoethanol | | |
| | | | 0.02 mM folic acid | | |
| | | | 12.5% FBS | | |
| | | | 12.5% HS | | |
| Mitochondria | — | 1 µg/mL | 15 µg/mL | 40 µg/mL | 100 µg/mL |

The following describes the culture flow for each cell. Firstly, each cell passage number at 4 to 10 is used for experiments. Each cell is cultured to 80% full of the Petri dish by a cell culture medium without mitochondria, the cell culture medium is removed, and then the cells are rinsed with phosphate buffered saline (PBS). Next, 0.25% trypsin is added to the Petri dish and reacted at 37° C. for 5 min, and the reaction is stopped by adding the cell culture medium into the Petri dish. Next, the cells and the cell culture medium in the Petri dish are moved to a centrifuge tube and centrifuged at 1000 rpm (300 g) for 5 min, and then the supernatant is removed. Next, the fresh cell culture medium is added into the centrifuge tube, and then the cells are counted. Next, ARPE-19 is cultured at a density of $2 \times 10^4$ cells per well by the cell culture composition of Embodiments 1-1 and 1-2 for 24 hours and for 48 hours. HepG2 is cultured at a density of $5 \times 10^4$ cells per well by the cell culture composition of Embodiments 2-1 and 2-2 for 24 hours. MDCK is cultured at a density of $5 \times 10^4$ cells per well by the cell culture composition of Embodiments 3-1 and 3-2 for 24 hours. Human tenocytes are cultured at a density of $2 \times 10^4$ cells per well by the cell culture composition of Embodiments 4-1 to 4-4 for 24 hours and for 48 hours. NK92MI is cultured at a density of $2 \times 10^4$ cells per well by the cell culture composition of Embodiments 5-1 to 5-4 for 24 hours and for 48 hours. After cell culture, the cells are washed with PBS, and the cell culture medium is replaced with the medium including Alamar blue and further cultured for 3 hours. After cell culturing with the medium including Alamar blue, the cell proliferation for each kind of cells are calculated by the fluorescence measured at OD530/595.

Figure 1B:
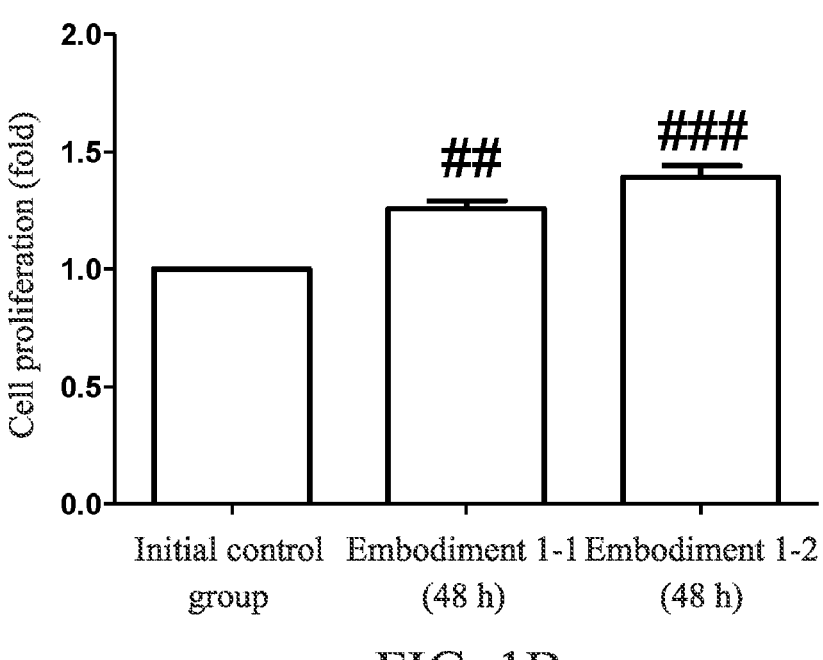
Figure 2:
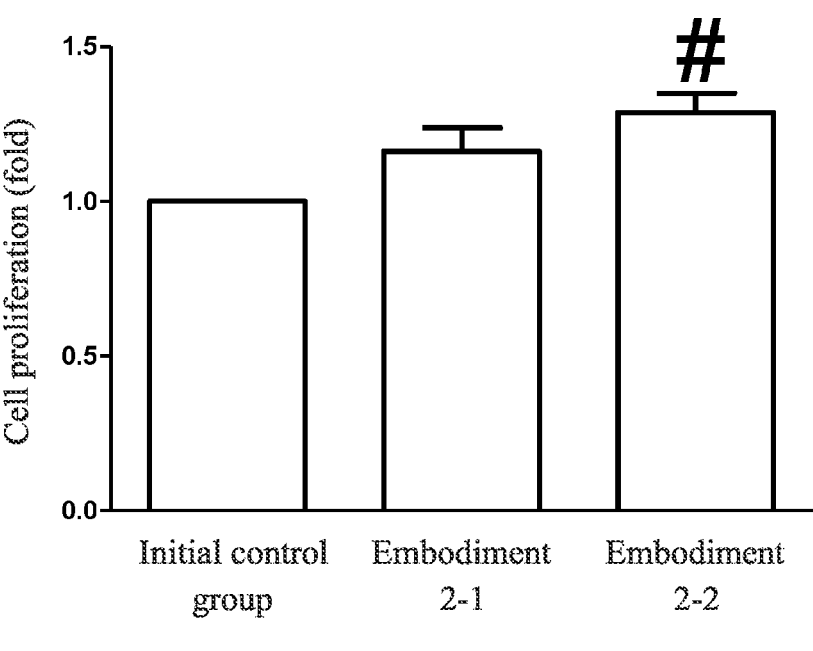
FIG. 2 shows the cell proliferation of HepG2 cultured by the cell culture composition according to the embodiment of the present disclosure for 24 hours.
Figure 3:
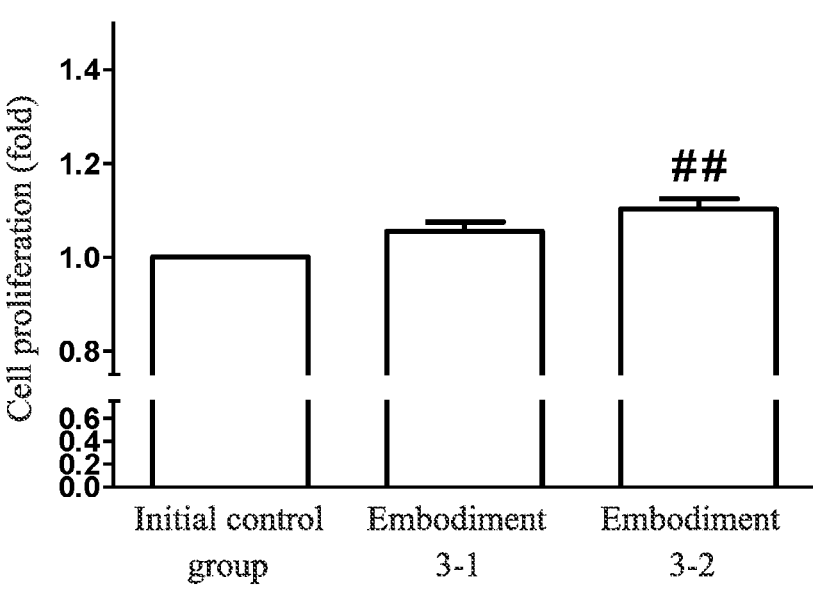
FIG. 3 shows the cell proliferation of MDCK cultured by the cell culture composition according to the embodiment of the present disclosure for 24 hours.
Figure 4:
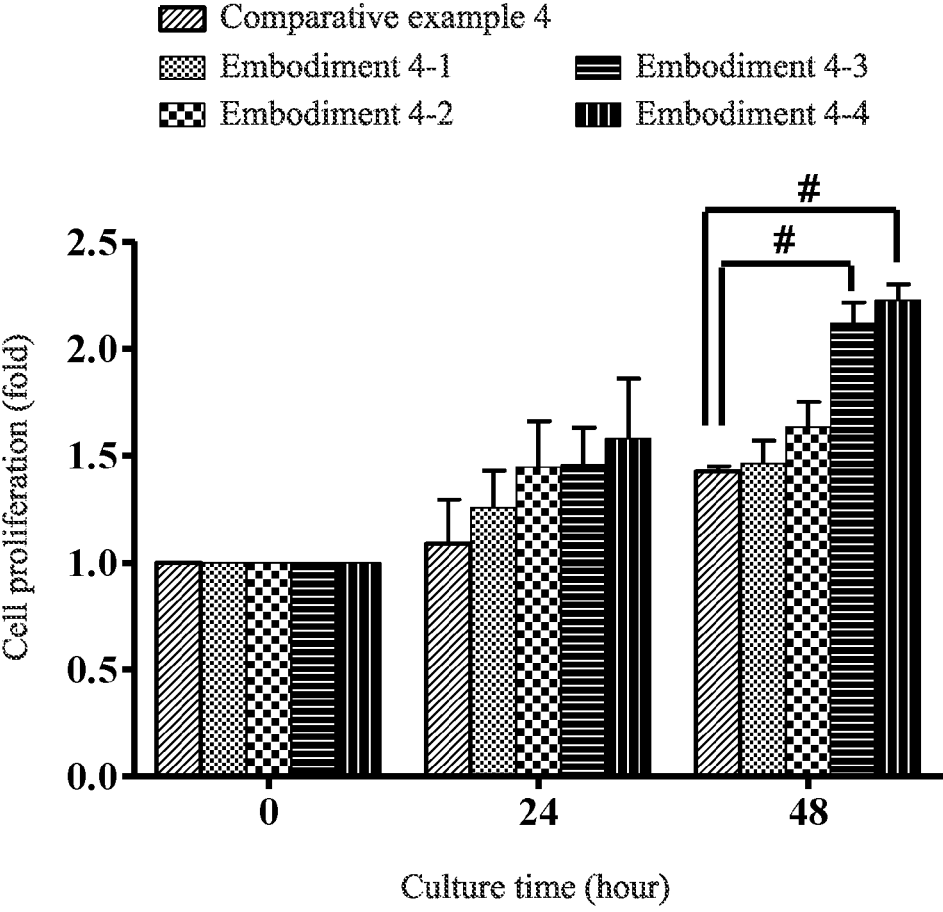
FIG. 4 shows the cell proliferation of human tenocytes cultured by the cell culture composition according to the embodiment of the present disclosure for 24 hours and for 48 hours.
Figure 5:
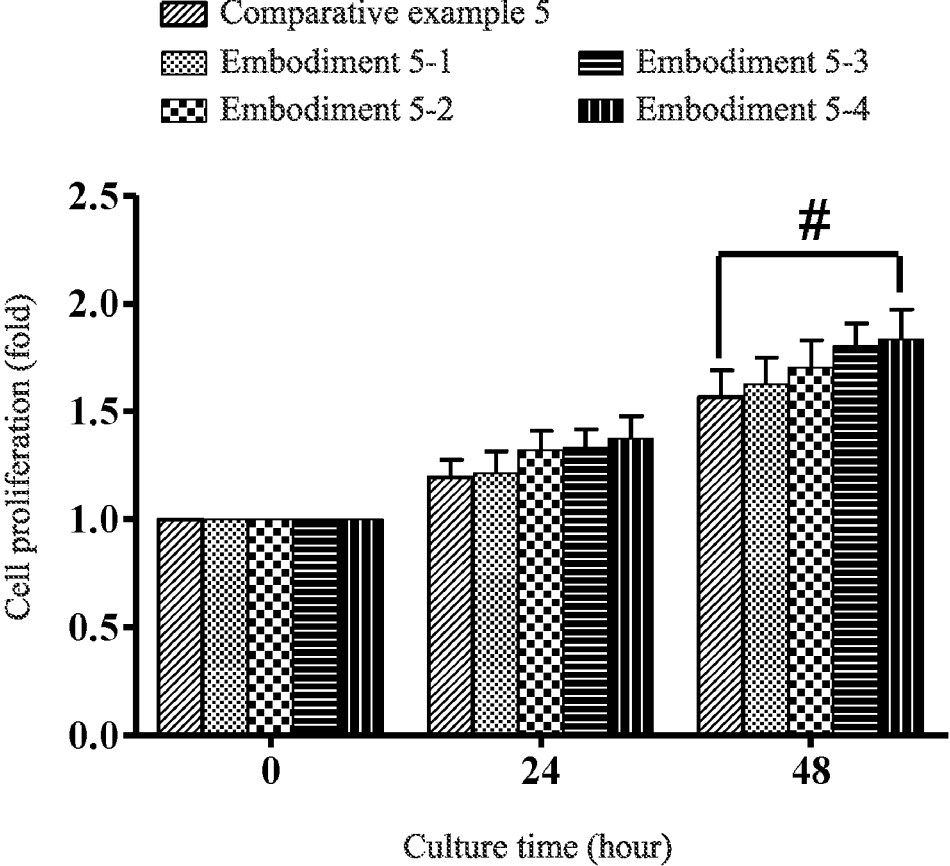
FIG. 5 shows the cell proliferation of NK92MI cultured by the cell culture composition according to the embodiment of the present disclosure for 24 hours and for 48 hours.

The experiment result of ARPE-19 is shown in Table 6 and FIGS. 1A and 1B. FIGS. 1A and 1B show the cell proliferation of ARPE-19 cultured by the cell culture composition according to the embodiment of the present disclosure for 24 hours (FIG. 1A) and for 48 hours (FIG. 1B). The experiment result of HepG2 is shown in Table 7 and FIG. 2. FIG. 2 shows the cell proliferation of HepG2 cultured by the cell culture composition according to the embodiment of the present disclosure for 24 hours. The experiment result of MDCK is shown in Table 8 and FIG. 3. FIG. 3 shows the cell proliferation of MDCK cultured by the cell culture composition according to the embodiment of the present disclosure for 24 hours. The experiment result of human tenocytes is shown in Table 9 and FIG. 4. FIG. 4 shows the cell proliferation of human tenocytes cultured by the cell culture composition according to the embodiment of the present disclosure for 24 hours and for 48 hours. The experiment result of NK92MI is shown in Table 10 and FIG. 5. FIG. 5 shows the cell proliferation of NK92MI cultured by the cell culture composition according to the embodiment of the present disclosure for 24 hours and for 48 hours. The initial control group is the cell number at the beginning of cell culture (at 0 hour) which is set as 1. The cell proliferation represents the fold of the cell number after cell culture compared to the cell number of the initial control group. The comparative example is the group cultured without the mitochondria. In FIGS. 1A to 3, # (P<0.05), ## (P<0.01), and ### (P<0.001) indicates a statistically significant difference compared to the initial control group. In FIGS. 4 and 5, # (P<0.05) indicates a statistically significant difference compared to the comparative example.

TABLE 6

ARPE-19

| | Mitochondria (μg/mL) | Cell proliferation at 24 hours (fold) | Cell proliferation at 48 hours (fold) |
|---|---|---|---|
| Embodiment 1-1 | 15 | 1.18 ± 0.16 | 1.25 ± 0.05 |
| Embodiment 1-2 | 40 | 1.26 ± 0.16 | 1.39 ± 0.07 |

TABLE 7

HepG2

| | Mitochondria (μg/mL) | Cell proliferation at 24 hours (fold) |
|---|---|---|
| Embodiment 2-1 | 15 | 1.16 ± 0.15 |
| Embodiment 2-2 | 40 | 1.28 ± 0.09 |

TABLE 8

MDCK

| | Mitochondria (μg/mL) | Cell proliferation at 24 hours (fold) |
|---|---|---|
| Embodiment 3-1 | 15 | 1.05 ± 0.05 |
| Embodiment 3-2 | 40 | 1.1 ± 0.05 |

TABLE 9

Human tenocytes

| | Mitochondria (μg/mL) | Cell proliferation at 24 hours (fold) | Cell proliferation at 48 hours (fold) |
|---|---|---|---|
| Comparative example 4 | — | 1.09 ± 0.21 | 1.42 ± 0.02 |
| Embodiment 4-1 | 1 | 1.26 ± 0.17 | 1.46 ± 0.09 |
| Embodiment 4-2 | 15 | 1.45 ± 0.22 | 1.63 ± 0.12 |
| Embodiment 4-3 | 40 | 1.46 ± 0.18 | 2.12 ± 0.10 |
| Embodiment 4-4 | 100 | 1.58 ± 0.28 | 2.23 ± 0.07 |

TABLE 10

NK92MI

| | Mitochondria (μg/mL) | Cell proliferation at 24 hours (fold) | Cell proliferation at 48 hours (fold) |
|---|---|---|---|
| Comparative example 5 | — | 1.19 ± 0.08 | 1.57 ± 0.13 |

TABLE 10-continued

| NK92MI | | | |
|---|---|---|---|
| | Mitochondria (µg/mL) | Cell proliferation at 24 hours (fold) | Cell proliferation at 48 hours (fold) |
| Embodiment 5-1 | 1 | 1.22 ± 0.08 | 1.63 ± 0.09 |
| Embodiment 5-2 | 15 | 1.32 ± 0.09 | 1.70 ± 0.13 |
| Embodiment 5-3 | 40 | 1.33 ± 0.08 | 1.81 ± 0.10 |
| Embodiment 5-4 | 100 | 1.37 ± 0.10 | 1.83 ± 0.14 |

The above experiment results show that the cell proliferation can be increased by culturing the cells using the cell culture composition including the mitochondria, and the cell proliferation is increased with the concentration of the mitochondria in the cell culture composition increased. This indicates the cell culture composition indeed contributes to cell growth. In addition, the increase of the cell proliferation is more significant as the culture time is increased, and it indicates the cell culture composition can stably contribute to cell growth.

Experiment 2: Decreasing Senescence Level of the Aged Stem Cells

In this experiment, the stem cells are induced to be aged by the advanced glycation end product (AGE), and the aged stem cells are cultured by the cell culture composition of the embodiments of the present disclosure. The effect of the cell culture composition on the aged stem cells is assessed by SA-(3-gal kit and, the senescence level is expressed by the proportion of the aged cells (%). The stem cells used in this experiment include adipose-derived stem cells (ADSC) and amniotic membrane stem cells (AMSC).

In the aged cells, senescence-associated beta-galactosidase (SA-(3-gal) is overexpressed, and thus SA-(3-gal may be a biomarker of cellular senescence. The senescence level of the stem cells is assessed by a SA-P-gal kit (Senescence (3-Galactosidase Staining Kit #9860, Cell Signaling Technology) in this experiment.

The detailed compositions of the cell culture composition of the embodiments used in this experiment are shown in Tables 11 and 12.

For ADSC, the culture medium may be Keratinocyte SFM (1X) (Catalog number: 17005042, Life Technologies), and the nutrient additives may include 10% FBS. The concentration of the mitochondria in the cell culture composition may be 1 µg/mL to 100 µg/mL, may be 5 µg/mL to 80 µg/mL, may be 15 µg/mL to 40 µg/mL, or may be 1 µg/mL, 15 µg/mL or 40 µg/mL.

For AMSC, the culture medium may be DMEM/F12 (Gibco), and the nutrient additives may include 10% FBS. The concentration of the mitochondria in the cell culture composition may be 1 µg/mL to 100 µg/mL, may be 5 µg/mL to 80 µg/mL, may be 15 µg/mL to 40 µg/mL, or may be 1 µg/mL, 15 µg/mL or 40 µg/mL.

TABLE 11

| | Cell ADSC | | | |
|---|---|---|---|---|
| Group | Comparative example 6 | Embodiment 6-1 | Embodiment 6-2 | Embodiment 6-3 |
| Culture medium | Keratinocyte SFM (1X) | | | |
| Nutrient additive | 10% FBS | | | |
| Mitochondria | — | 1 µg/mL | 15 µg/mL | 40 µg/mL |

TABLE 12

| | Cell AMSC | | | |
|---|---|---|---|---|
| Group | Comparative example 7 | Embodiment 7-1 | Embodiment 7-2 | Embodiment 7-3 |
| Culture medium | DMEM/F12 | | | |
| Nutrient additive | 10% FBS | | | |
| Mitochondria | — | 1 µg/mL | 15 µg/mL | 40 µg/mL |

The following describes the culture flow for the stem cell. Firstly, the stem cells passage number at 10 is used for experiments. The stem cells are cultured to 80% full of the Petri dish by a cell culture medium without mitochondria, the cell culture medium is removed, and then the stem cells are rinsed with phosphate buffered saline (PBS). Next, 0.25% trypsin is added into the Petri dish and reacted at 37° C. for 5 min, and then the reaction is stopped by adding the cell culture medium. Next, the cells and the cell culture medium in the Petri dish are moved to a centrifuge tube and centrifuged at 1000 rpm (300 g) for 5 min, and then the supernatant is removed. Next, the fresh cell culture medium is added into the centrifuge tube, and then the cells are counted. Next, the stem cells are cultured at a density of $1 \times 10^4$ cells per well for 24 hours. Next, AGE is added to the well, and the stem cells are cultured in the cell culture medium including 400 µg/mL AGE for 4 hours. Next, the cell culture medium including AGE is removed from the well, and the cell culture composition of the embodiment is added into the well. The stem cells are cultured in the cell culture composition including the mitochondria with different concentrations for 24 hours. The concentration of the mitochondria in the cell culture composition is 0 µg/mL, 1 µg/mL, 15 µg/mL, or 40 µg/mL. After cell culture, the stem cells are washed with PBS, and the senescence level of the stem cells is assessed by SA-(3-gal kit.

Figures 6, 7:
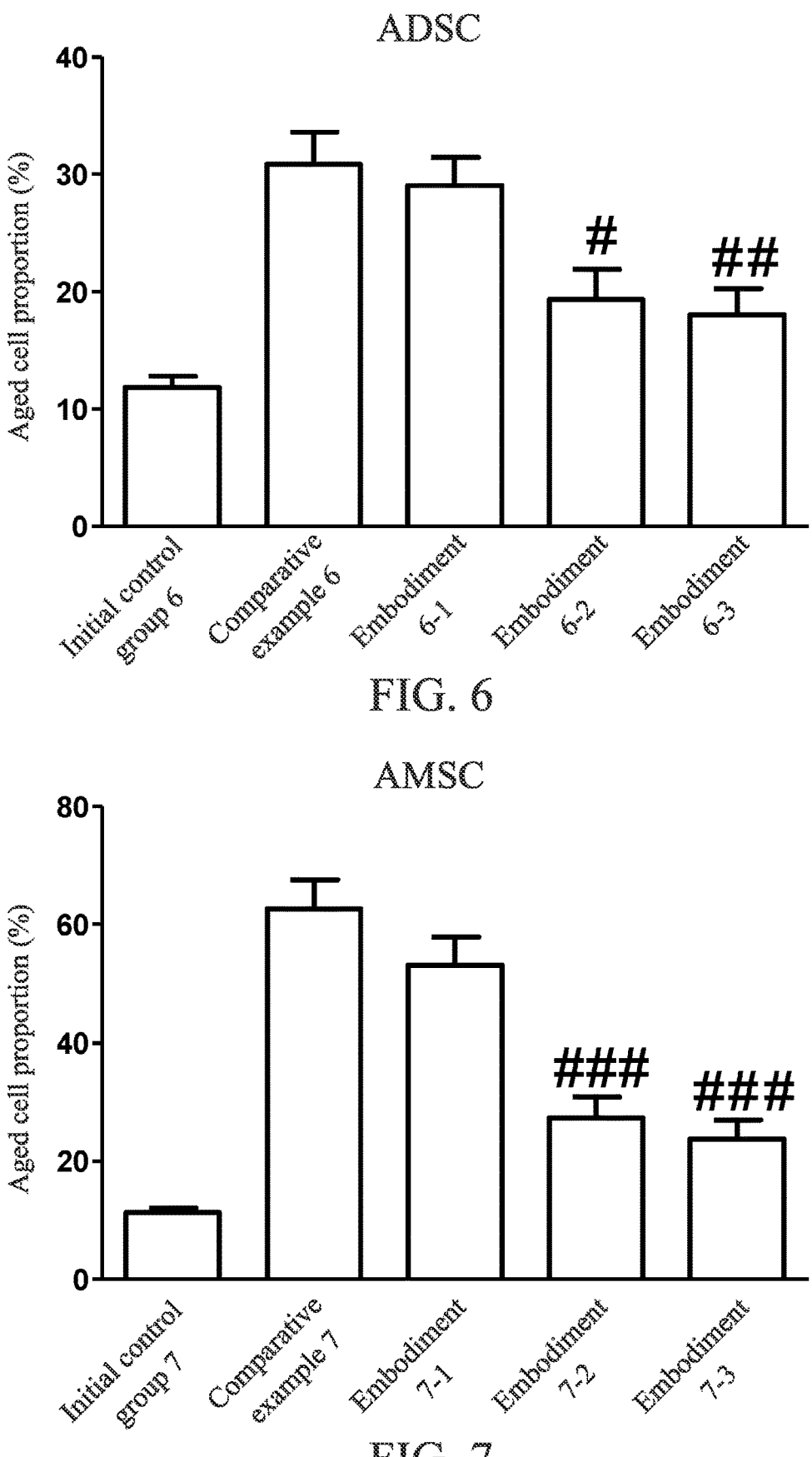
FIG. 6 shows the aged cell proportion of the aged ADSC cultured by the cell culture composition according to the embodiment of the present disclosure.
FIG. 7 shows the aged cell proportion of the aged AMSC cultured by the cell culture composition according to the embodiment of the present disclosure.

The experiment result of ADSC is shown in Table 13 and FIG. 6. FIG. 6 shows the aged cell proportion of the aged ADSC cultured by the cell culture composition according to the embodiment of the present disclosure. The experiment result of AMSC is shown in Table 14 and FIG. 7. FIG. 7 shows the aged cell proportion of the aged AMSC cultured by the cell culture composition according to the embodiment of the present disclosure. The comparative example is the group aged by AGE but without treating with mitochondria. The control group is the group without being aged by AGE and without treating with mitochondria. The aged cell proportion is the percentage of the amount of the aged cells to the amount of all cells in a unit area and represents the senescence level. In FIGS. 6 and 7, the vertical axis is the aged cell proportion (%), # ($P < 0.05$), ## ($P < 0.01$), and ###

(P<0.001) indicates a statistically significant difference compared to the comparative example.

TABLE 13

|  | ADSC | | |
|  | AGE (μg/mL) | Mitochondria (μg/mL) | Aged cell proportion (%) |
| --- | --- | --- | --- |
| Control group 6 | — | — | 11.8 ± 2.32 |
| Comparative example 6 | 400 | — | 30.8 ± 6.7 |
| Embodiment 6-1 |  | 1 | 29 ± 5.9 |
| Embodiment 6-2 |  | 15 | 19.33 ± 6.25 |
| Embodiment 6-3 |  | 40 | 18 ± 5.55 |

TABLE 14

|  | AMSC | | |
|  | AGE (μg/mL) | Mitochondria (μg/mL) | Aged cell proportion (%) |
| --- | --- | --- | --- |
| Control group 7 | — | — | 11.3 ± 1.75 |
| Comparative example 7 | 400 | — | 62.67 ± 12.03 |
| Embodiment 7-1 |  | 1 | 53.17 ± 11.57 |
| Embodiment 7-2 |  | 15 | 27.33 ± 8.5 |
| Embodiment 7-3 |  | 40 | 23.67 ± 7.92 |

The above experiment results show that the aged cell proportion can be decreased by culturing the aged stem cells using the cell culture composition including the mitochondria, and the aged cell proportion decreases with the increase in the concentration of the mitochondria. This indicates the cell culture composition including the mitochondria indeed contributes to improving the cell growth of the damaged or aged stem cells and improving the function of the damaged or aged stem cells.

Experiment 3: Cell Culture Composition Including Platelets

In this experiment, the platelets are further added to the cell culture composition including the mitochondria, and the fibroblasts (CCD-996SK) are cultured by the cell culture composition including the mitochondria and the platelets as the cell culture medium. In addition, the effect of the cell culture composition on cell growth in this experiment is assessed by Alamar blue cell viability reagent kit and expressed by the cell proliferation (fold).

The following describes the preparation of the platelets used in this experiment. Firstly, some blood is drawn to a blood collection tube or a centrifuge tube, and the blood collection tube may be, for example, CPT tube (BD Vacutainer® CPT™ Cell Preparation Tube, REF362761). Next, the blood is centrifuged, for example, at 1500 g for 10 min, to stratify the blood to form an erythrocyte layer, a colloidal layer, a buffy coat layer, and a plasma layer. The buffy coat layer is collected in another centrifuge tube, wherein the buffy coat layer includes monocytes and platelets. Next, the buffy coat layer is mixed uniformly with HEP buffer (140 mM NaCl, 2.7 mM KCl, 3.8 mM HEPES, and 5 mM EGTA, pH 7.4) at a ratio of 1:1, and 1 μM of Prostaglandin E1 is added to prevent the platelets from activation. Next, the buffy coat layer is centrifuged at 100 g for 15 to 20 min to precipitate the monocytes and the residual erythrocytes, and the supernatant including the platelets is collected in another centrifuge tube. Next, the supernatant including the platelets is centrifuged at 800 g for 15 to 20 min to precipitate the platelets. The supernatant is removed, and the platelet pellets are rinsed twice with a wash buffer (10 mM sodium citrate, 150 mM NaCl, 1 mM EDTA, and 1% (w/v) dextrose). Next, the platelet pellets are resuspended with Tyrode's buffer (134 mM NaCl, 12 mM NaHCO$_3$, 2.9 mM KCl, 0.34 mM Na$_2$HPO$_4$, 1 mM MgCl$_2$, and 10 mM HEPES, pH 7.4), and the platelets are counted by a hemocytometer. The prepared platelets may be stored at 20° C. to 24° C. until added to the cell culture composition, but it is preferable to use them immediately after preparation.

The detailed compositions of the cell culture composition of the embodiments used in this experiment are shown in Tables 15 and 16.

For CCD-996SK, the culture medium may be DMEM with 2 mM glutamine (Gibco, 10566016), and the nutrient additives may include 10% FBS. The concentration of the mitochondria in the cell culture composition may be 1 μg/mL to 100 μg/mL, may be 5 μg/mL to 80 μg/mL, may be 15 μg/mL to 40 μg/mL, or may be 1 μg/mL, 15 μg/mL or 40 μg/mL. The platelets in the cell culture composition may be $1×10^6$ to $1×10^8$ particles per mL, or may be $1×10^6$ particles per mL, $1×10^7$ particles per mL or $1×10^8$ particles per mL.

TABLE 15

|  | Cell CCD-996SK | | |
| Group | Comparative example 8-1 | Comparative example 8-2 | Comparative example 8-3 |
| --- | --- | --- | --- |
| Culture medium | DMEM/2 mM glutamine | | |
| Nutrient additive | 10% FBS | | |
| Platelets | $1 × 10^6$ particles per mL | $1 × 10^7$ particles per mL | $1 × 10^8$ particles per mL |
| Mitochondria | — | — | — |

TABLE 16

|  | Cell CCD-996SK | | | | |
| Group | Control group 8 | Embodiment 8-1 | Embodiment 8-2 | Embodiment 8-3 | Embodiment 8-4 |
| --- | --- | --- | --- | --- | --- |
| Culture medium | DMEM/2 mM glutamine | | | | |
| Nutrient additive | 10% FBS | | | | |

TABLE 16-continued

| | Cell CCD-996SK | | | | |
| --- | --- | --- | --- | --- | --- |
| Group | Control group 8 | Embodiment 8-1 | Embodiment 8-2 | Embodiment 8-3 | Embodiment 8-4 |
| Platelets | — | — | — | — | $1 \times 10^6$ particles per mL |
| Mitochondria | — | 1 µg/mL | 15 µg/mL | 40 µg/mL | 40 µg/mL |

Please refer to Experiment 1 for the culture flow. For cell counting, CCD-996SK is cultured at a density of $1.5 \times 10^4$ cells per well by the cell culture composition of the control group, the comparative examples, and Embodiments 8-1 to 8-4 for 24 hours. After cell culture, the cells are washed with PBS, and the cell culture medium is replaced with the medium including Alamar blue and further cultured for 3 hours. After cell culturing with the medium including Alamar blue, the cell proliferation is calculated by the fluorescence measured at OD530/595.

Figure 8:
FIG. 8 shows the cell proliferation of CCD-996SK cultured by the cell culture composition of the comparative embodiments that only includes platelets for 24 hours and for 48 hours.
Figure 8:
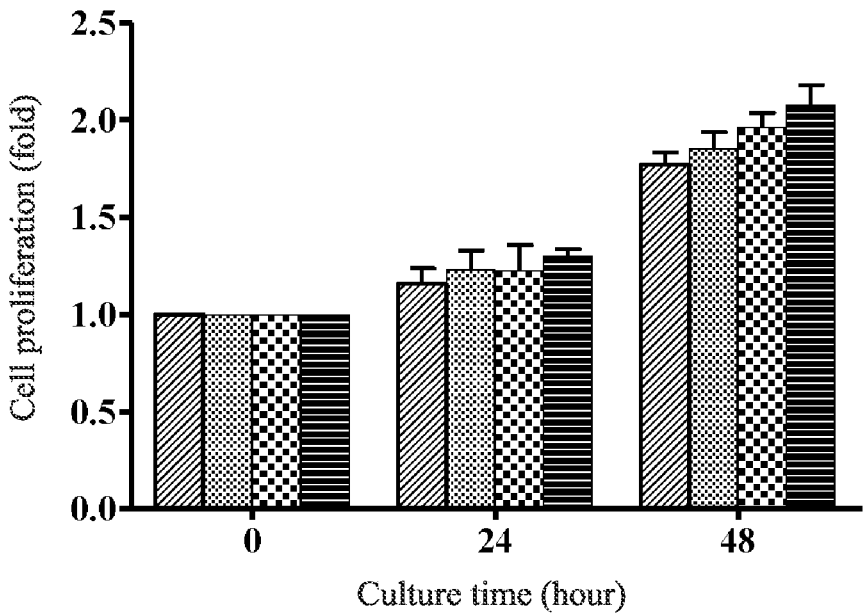
Figure 9:
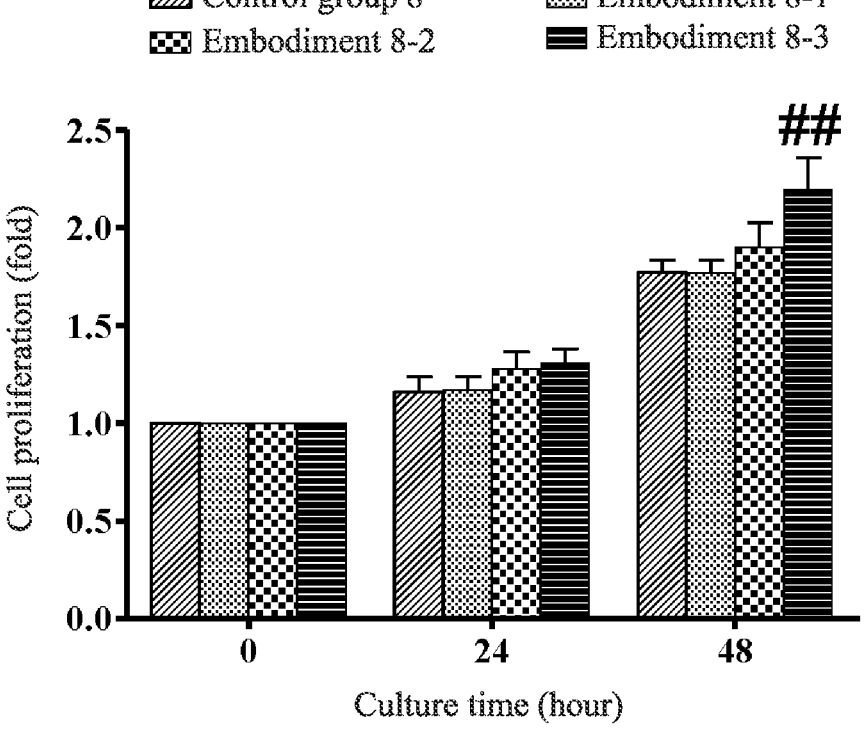
FIG. 9 shows the cell proliferation of CCD-996SK cultured by the cell culture composition of the embodiments that only includes mitochondria for 24 hours and for 48 hours.
Figure 10:
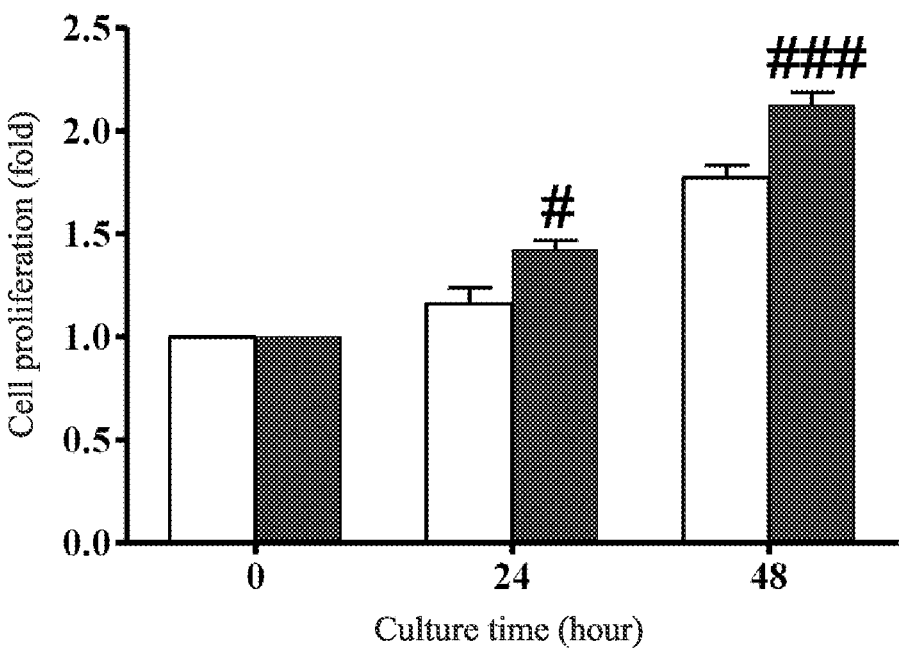
FIG. 10 shows the cell proliferation of CCD-996SK cultured by the cell culture composition of the embodiment that includes mitochondria and platelets for 24 hours and for 48 hours.

The experiment result of CCD-996SK is shown in Table 17 and FIGS. 8 to 10. FIG. 8 shows the cell proliferation of CCD-996SK cultured by the cell culture composition of the comparative examples that only includes platelets for 24 hours and for 48 hours. FIG. 9 shows the cell proliferation of CCD-996SK cultured by the cell culture composition of the embodiments that only includes mitochondria for 24 hours and for 48 hours. FIG. 10 shows the cell proliferation of CCD-996SK cultured by the cell culture composition of the embodiment that includes mitochondria and platelets for 24 hours and for 48 hours. The initial control group is the cell number at the beginning of cell culture (at 0 hour) which is set as 1. The cell proliferation represents the fold of the cell number after cell culture compared to the cell number of the initial control group. The comparative example is the group cultured with platelets but without the mitochondria. The control group is the group cultured without both mitochondria and platelets. In FIGS. 8 to 10, # ($P<0.05$), ## ($P<0.01$), and ### ($P<0.001$) indicate a statistically significant difference compared to the control group.

TABLE 17

| | CCD-996SK | | | |
| --- | --- | --- | --- | --- |
| | Mitochondria (µg/mL) | Platelets (cells) | Cell proliferation at 24 hours (fold) | Cell proliferation at 48 hours (fold) |
| Control group 8 | — | — | 1.16 ± 0.08 | 1.77 ± 0.06 |
| Comparative example 8-1 | — | $1 \times 10^6$ | 1.20 ± 0.06 | 1.85 ± 0.10 |
| Comparative example 8-2 | — | $1 \times 10^7$ | 1.23 ± 0.13 | 1.96 ± 0.07 |
| Comparative example 8-3 | — | $1 \times 10^8$ | 1.30 ± 0.04 | 2.08 ± 0.10 |
| Embodiment 8-1 | 1 | — | 1.17 ± 0.06 | 1.77 ± 0.07 |
| Embodiment 8-2 | 15 | — | 1.28 ± 0.08 | 1.90 ± 0.12 |
| Embodiment 8-3 | 40 | — | 1.31 ± 0.07 | 2.20 ± 0.16 |
| Embodiment 8-4 | 40 | $1 \times 10^6$ | 1.42 ± 0.05 | 2.13 ± 0.06 |

According to the above experiment results, the comparative examples show that the cell proliferation can be increased by adding the platelets to the cell culture medium, and the cell proliferation increases with the increase in the amount of the platelets. Embodiments 8-1 to 8-3 show that the cell proliferation can be increased by culturing the cells using the cell culture composition including the mitochondria, and the cell proliferation increases with the increase in the concentration of the mitochondria. This indicates the cell culture composition including the mitochondria indeed contributes to cell growth. Comparative example 8-1 and Embodiments 8-1 and 8-4 show that the cell proliferation can be further increased by culturing the cells using the cell culture composition including the mitochondria and the platelets. Embodiments 8-3 and 8-4 confirm in the case that the concentration of the mitochondria is 40 µg/mL, the cell proliferation can be further increased by adding $1 \times 10^6$ of the platelets to the cell culture medium. Embodiment 8-4 and Comparative example 8-1 confirm in the case that the amount of the platelets is $1 \times 10^6$, the cell proliferation can be further increased by adding 40 µg/mL of the mitochondria to the cell culture medium, and the cell proliferation of Embodiment 8-4 in which the amount of the platelets is $1 \times 10^6$ even exceeds that of Comparative example 8-3 in which the amount of the platelets is $1 \times 10^8$. Accordingly, compared to the cell culture composition including only platelets or only mitochondria, the cell culture composition including both the mitochondria and the platelets has a synergistic effect on increasing the cell proliferation. In addition, the increase in the cell proliferation is more significant as the culture time increases, and it indicates the cell culture composition can stably contribute to cell growth. Here, it is especially stated that the cell proliferation at 48 hours of Embodiment 8-4 is slightly lower than that of Embodiment 8-3 because the cells grow to saturation. The total amount of the cells should be roughly equal when the cells grow to saturation, and thus, the difference in the cell proliferation at 48 hours is not obvious.

Experiment 4: Cell Culture Composition Including Complement Component (C3)

In this experiment, C3 (Sigma-Aldrich, 204885) is further added to the cell culture composition including the mitochondria, and ARPE-19 is cultured by the cell culture composition including the mitochondria and C3 as the cell culture medium. In addition, the effect of the cell culture composition on cell growth in this experiment is assessed by Alamar blue cell viability reagent kit and expressed by the cell proliferation (fold).

The detailed compositions of the cell culture composition of the embodiments used in this experiment are shown in Table 18.

For ARPE-19, the culture medium may be DMEM/F12 (Gibco), and the nutrient additives may include 2.5 mM glutamine, 15 mM HEPES, 0.5 mM sodium pyruvate, 1200 mg/L sodium bicarbonate, and 10% FBS. The concentration of the mitochondria in the cell culture composition may be 1 μg/mL to 100 μg/mL, may be 5 μg/mL to 80 μg/mL, may be 15 μg/mL to 40 μg/mL, or may be 15 μg/mL. The concentration of C3 in the cell culture composition may be 0.1 μg/mL to 20 μg/mL, or may be 10 μg/mL.

TABLE 18

| Group | Cell ARPE-19 | |
| --- | --- | --- |
| | Control group 9 | Embodiment 9-1 |
| Culture medium | DMEM/F12 | |
| Nutrient additive | 2.5 mM glutamine 15 mM HEPES 0.5 mM sodium pyruvate 1200 mg/L sodium bicarbonate 10% FBS | |
| C3 | — | 10 μg/mL |
| Mitochondria | — | 15 μg/mL |

Please refer to Experiment 1 for the culture flow. For cell counting, ARPE-19 is cultured at a density of $2 \times 10^4$ cells per well by the cell culture composition of the control group and the embodiments for 24 hours and for 48 hours. The concentration of the mitochondria in the well is 15 μg/mL, and the concentration of C3 in the well is 10 μg/mL. After cell culture, the cells are washed with PBS, and the cell culture medium is replaced with the medium including Alamar blue and further cultured for 3 hours. After cell culture with the medium including Alamar blue, the cell proliferation is calculated by the fluorescence measured at OD530/595.

Figure 11:
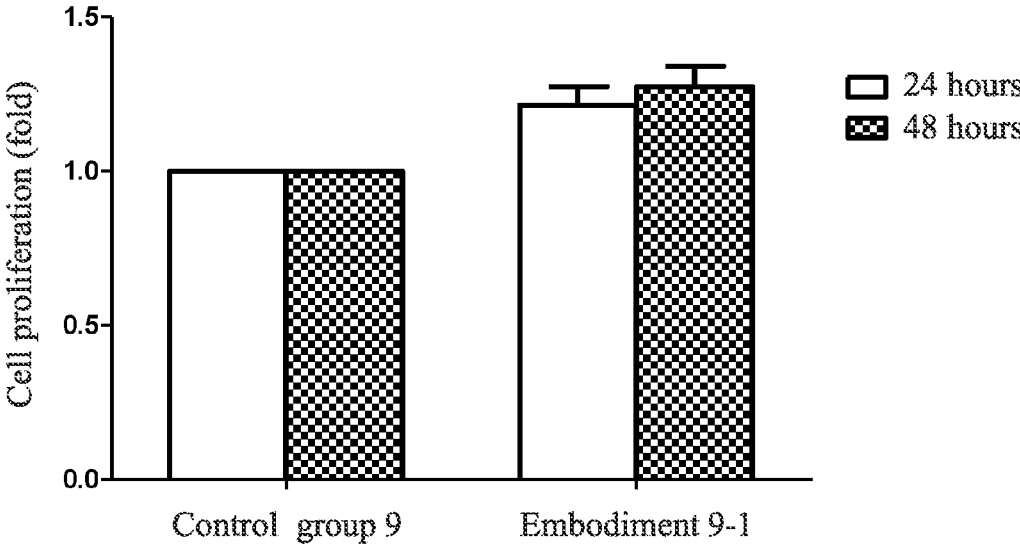
FIG. 11 shows the cell proliferation of ARPE-19 cultured by the cell culture composition of the embodiment that includes mitochondria and C3 for 24 hours and for 48 hours.

The experiment result of ARPE-19 is shown in Table 19 and FIG. 11. FIG. 11 shows the cell proliferation of ARPE-19 cultured by the cell culture composition of the embodiment that includes mitochondria and C3 for 24 hours and for 48 hours. The control group is the group cultured without mitochondria and C3 which is set as 1. The cell proliferation represents the fold of the cell number after cell culture compared to the cell number of the control group.

TABLE 19

| | ARPE-19 | | | |
| --- | --- | --- | --- | --- |
| | Mitochondria (μg/mL) | C3 (μg/mL) | Cell proliferation at 24 hours (fold) | Cell proliferation at 48 hours (fold) |
| Control group 9 | — | — | 1 | 1 |
| Example 9-1 | 15 | 10 | 1.22 | 1.28 |

The above experiment results show that the cell proliferation can be further increased by culturing the cells by the cell culture composition including the mitochondria and C3.

In addition, the increase in the cell proliferation is more significant as the culture time increases, and it indicates the cell culture composition can stably contribute to cell growth.

In view of the above description, the addition of mitochondria in the cell culture medium can help cell growth and increase cell proliferation. For the damaged or aged cells, the cell culture composition according to the present disclosure can also improve the growth of the damaged or aged cells and decrease the proportion of the aged cells. In addition, the cell culture composition according to the present disclosure can also improve the function of the damaged or aged cells. For academic, the cell culture composition according to the present disclosure ensures the efficiency and stability of cell growth and is helpful for the subsequent experiment and research to lay a foundation for scientific development and biological research. For industry, the cell culture composition according to the present disclosure ensures the efficiency and stability of cell growth and is helpful for productivity and yield so that the cost of cell culture can be reduced and the quality of the production can be controlled to maximize benefits.

What is claimed is:

1. A method for promoting cell growth, comprising culturing cells in a cell culture composition, wherein the cell culture composition comprises a culture medium and mitochondria isolated from cells, and the cell culture composition comprises 15 μg to 40 μg of the mitochondria per milliliter.

2. The method of claim 1, wherein the cell growth comprises growing retinal cells, hepatocytes, kidney cells, tenocytes, skin cells, or immunocytes.

3. The method of claim 2, wherein the immunocytes are CD56+CD3− natural killer cells.

4. The method of claim 1, wherein the cell culture composition further comprises $1 \times 10^6$ to $1 \times 10^8$ of platelets per milliliter.

5. The method of claim 1, wherein the cell culture composition further comprises 0.1 μg to 20 μg of complement component 3 (C3) per milliliter.

6. A method for improving the function of the damaged or aged cells, comprising culturing damaged or aged cells in a cell culture composition, wherein the cell culture composition comprises a culture medium and mitochondria isolated from cells, and the cell culture composition comprises 15 μg to 40 μg of the mitochondria per milliliter.

7. The method of claim 6, wherein the damaged or aged cells are stem cells.

8. The method of claim 7, wherein the stem cells cultured in the cell culture composition are mesenchymal stem cells.

9. The method of claim 7, wherein the stem cells are CD90+CD34− stem cells.

10. The method of claim 6, wherein the cell culture composition further comprises $1 \times 10^6$ to $1 \times 10^8$ of platelets per milliliter.

11. The method of claim 6, wherein the cell culture composition further comprises 0.1 μg to 20 μg of complement component 3 (C3) per milliliter.

* * * * *